United States Patent
Liu et al.

(10) Patent No.: US 10,350,568 B2
(45) Date of Patent: Jul. 16, 2019

(54) MEMBRANE-FORMING COMPOSITION, SOFT AND HARD CAPSULES PREPARED BASED ON THIS COMPOSITION AND THE PREPARATION METHODS

(71) Applicant: JIANGSU LEFAN CAPSULE CO., LTD., Zhenjiang (CN)

(72) Inventors: Peiyong Liu, Zhenjiang (CN); Peng Lei, Zhenjiang (CN); Li Wang, Zhenjiang (CN); Xiao Dou, Zhenjiang (CN); Xudong Zhu, Zhenjiang (CN); Yichi Zhang, Zhenjiang (CN)

(73) Assignee: JIANGSU LEFAN CAPSULE CO., LTD., Zhenjiang (CN)

( * ) Notice: Subject to any disclaimer, the term of this patent is extended or adjusted under 35 U.S.C. 154(b) by 79 days.

(21) Appl. No.: 15/546,366

(22) PCT Filed: Aug. 2, 2016

(86) PCT No.: PCT/CN2016/092859
§ 371 (c)(1),
(2) Date: Jul. 26, 2017

(87) PCT Pub. No.: WO2017/197774
PCT Pub. Date: Nov. 23, 2017

(65) Prior Publication Data
US 2018/0154327 A1    Jun. 7, 2018

(30) Foreign Application Priority Data

May 19, 2016  (CN) .......................... 2016 1 0334512
Jul. 13, 2016  (CN) .......................... 2016 1 0552604

(51) Int. Cl.
| | |
|---|---|
| *B01J 13/04* | (2006.01) |
| *B01J 13/20* | (2006.01) |
| *B29C 41/00* | (2006.01) |
| *B29C 41/14* | (2006.01) |
| *B29L 31/00* | (2006.01) |

(52) U.S. Cl.
CPC ............ *B01J 13/046* (2013.01); *B01J 13/04* (2013.01); *B01J 13/206* (2013.01); *B29C 41/003* (2013.01); *B29C 41/14* (2013.01); *B29K 2005/00* (2013.01); *B29L 2031/7174* (2013.01)

(58) Field of Classification Search
CPC combination set(s) only.
See application file for complete search history.

(56) References Cited

U.S. PATENT DOCUMENTS

2005/0031853 A1    2/2005  Scott et al.

FOREIGN PATENT DOCUMENTS

| CN | 101069677 A | 11/2007 |
|---|---|---|
| CN | 101317831 A | 12/2008 |
| CN | 101438782 A | 5/2009 |
| CN | 101579326 A | 11/2009 |
| CN | 102499910 A | 6/2012 |
| CN | 102805871 A | 12/2012 |
| WO | WO 02/34238 A2 | 5/2002 |
| WO | WO 2006/064235 A2 | 6/2006 |

OTHER PUBLICATIONS

Full English Machine Translation of CN 102805871.*
International Search Report (PCT/ISA/210) dated Feb. 20, 2017, by the State Intellectual Property Office of China as the International Searching Authority for International Application No. PCT/CN2016/092859.
Written Opinion (PCT/ISA/237) dated Feb. 20, 2017, by the State Intellectual Property Office of China as the International Searching Authority for International Application No. PCT/CN2016/092859.

* cited by examiner

*Primary Examiner* — Hasan S Ahmed
(74) *Attorney, Agent, or Firm* — Buchanan Ingersoll & Rooney PC

(57) ABSTRACT

A membrane-forming composition, soft and hard capsules prepared based on the composition and the preparation methods are described. The membrane-forming composition includes pullulan polysaccharide, gellan gum, amino acid moisturizing agent, anti-hygroscopic agent and so on. It is suitable for the fabrication of hard or soft capsules. The membrane-forming composition can gelate without alkali metal ions. It has a high moisture retention rate which makes it not easy to take up moisture and turn soft in high humid environment, and it will not turn yellow during long time storage. Furthermore, the membrane-forming composition is made up of pure natural materials.

4 Claims, No Drawings

MEMBRANE-FORMING COMPOSITION, SOFT AND HARD CAPSULES PREPARED BASED ON THIS COMPOSITION AND THE PREPARATION METHODS

TECHNICAL FIELD OF INVENTION

This invention relates to the field of capsule technology, especially a kind of membrane-forming compound, soft and hard capsules prepared based on this compound and the preparation methods.

TECHNICAL BACKGROUND OF INVENTION

Hollow capsules have been widely used in industries including pharmacy, food, cosmetics and so on. It has been extensively developed and applied.

Most of hollow capsules nowadays are fabricated using gelatin as main molding gel. However, a lot quality defects are shown during the application process due to the characteristics of gelatin itself. For example, gelatin molecules may generate a tough, flexible and water insoluble membrane through self-oxidation reaction or intramolecular and intermolecular cross-linking reactions with functional groups such as aldehyde group. This membrane may hinder the drug release and it will result in the disqualification of capsule disintegration. Besides, when using gelatin as main molding gel, it is prone to appear quality defects, such as oil leakage, adhesion and further oxidation of the oxidizable component in long time storage. Moreover, with the increase of religion and vegetarianism, as well as the successive appearance of BSE (bovine spongiform encephalopathy), foot-and-mouth disease events all over the word, people begin to feel unsafe about the gel made from bones and skin of cows and other animals. So it is very necessary to develop non-animal capsule shells. At the present stage, there are three kinds of widely investigated non-animal capsule shells. The first one is mainly made of water soluble cellulose derivatives, such as HPMC (hydroxypropyl methylcellulose) hollow capsules, but it has high oxygen permeability, poor disintegrating stability and appearance properties. The second one is mainly made of starch. However, it has poor friability and cannot hold liquids. The third one is mainly made of polysaccharide polymers, among which hollow capsules made of pullulan polysaccharide are mostly studied. This kind of capsule has low oxygen permeability, good transparency and short disintegration time, thus it becomes a research hotspot.

Domestic and foreign experts and scholars provide a lot of methods to improve the quality of capsules containing pullulan polysaccharide. For example, it is proposed in U.S. patent Ser. No. 10/941,182 that pullulan polysaccharide hard or soft capsules can be made using pullulan polysaccharide as main ingredient and surfactants, gels, cationic coagulant aids and chelating agents as additives. Chinese patent NO. CN101069677 shows that hollow pullulan polysaccharide capsules can be made using pullulan polysaccharide as main ingredient and gels, cationic coagulant aids, surfactants and moisturizing agents as additives. Chinese patent NO. CN201110420285.0 also proposed that hollow pullulan polysaccharide capsules can be made using the pullulan polysaccharide as main ingredient and hydrophilic gels, plasticizer, surfactants and moisturizing agents as additives.

Although the methods proposed above have some effects on improving the quality of pullulan polysaccharide capsules, there are still some shortages of pullulan polysaccharide capsules in practical use. For example, the pullulan polysaccharide capsules have poor storage stability. It will dehydrate and get brittle and dark after long time storage. The requirement of the humidity of storage environment is very strict. When the humidity is slightly higher, the capsule will turn softer. What's more, alkali metal ions are introduced into the preparation process of pullulan polysaccharides capsules, which will influence the disintegration of the capsules. So, further improvement is needed.

CONTENTS OF INVENTION

Aiming at the technical problems stated above, the solution proposed by this invention provides a membrane-forming compound which can gelate without alkali metal ions, retain moisture during long time storage and stay water non-absorbing under the environment of high humidity. Besides, good interactions between the components of the compound are obtained and it results in an improvement in the performance of the membrane-forming compound. In another word, a good overall performance is achieved with fewer components. Furthermore, hard or soft capsules are fabricated using this membrane-forming compound, and both of their properties are improved.

The other purpose of this invention is to provide a pure natural membrane-forming compound. That is to say, the compound stated in this invention completely consists of pure natural materials, and it meets people's demand for nature.

The purpose stated above is implemented by the following technical scheme:

The membrane-forming compound contains pullulan polysaccharide, gellan gum and methylglycine-proline moisturizing agent.

The membrane-forming compound stated above may also contain an anti-hygroscopic agent.

The preferred gellan gum in the membrane-forming compound stated above is high acyl gella gum.

The anti-hygroscopic agent in membrane-forming compound described above has one or combination of stearic acid and lauric acid in any proportion.

The membrane-forming compound stated above may contain plasticizer. Furthermore, the plasticizer may be glycerin.

A kind of hard capsule containing pullulan polysaccharide is prepared using the membrane-forming compound stated above. Its raw materials consist of following components:
pullulan polysaccharide 76-90 weight percent, gellan gum 0.5-4 weight percent, methylglycine-proline moisturizing agent 0.05-2 weight percent, anti-hygroscopic agent 0-1 weight percent.

A kind of soft capsule containing pullulan polysaccharide is prepared using the membrane-forming compound stated above, its raw materials consist of following components:
pullulan polysaccharide 20-55 weight percent, gellan gum 0.5-4 weight percent, methylglycine-proline moisturizing agent 0.05-2 weight percent, anti-hygroscopic agent 0-1 weight percent, plasticizer 6-40 weight percent.

The procedures of the preparation method of hard capsule containing pullulan polysaccharide stated above are as follows:

(1) Weigh the following components by ratio: pullulan polysaccharide 76-90 weight percent, gellan gum 0.5-4 weight percent, methylglycine-proline moisturizing agent 0.05-2 weight percent, anti-hygroscopic agent 0-1 weight percent.

(2) Add 300-550 weight percent purified water (>80° C.) into the reaction tank at ambient pressure, turn on the blender, set the agitation speed at 40-60 r/min, add gellan gum, amino acid moisturizing agent and antihygroscopic agent into the water, stir until the components are well-dispersed.

(3) Add pullulan polysaccharide, stir until it is completely dissolved, keep the gel solution temperature at 70-90° C. for 2-8 h and vacuumize for 20-40 min.

(4) Cool down the gel solution and keep the temperature at 35-75° C., dip the mold into the gel solution and make capsule shells, dry at 27-29° C. for 100-180 min. Finally, hard capsule containing pullulan polysaccharide is obtained.

The procedures of the preparation method of soft capsule containing pullulan polysaccharide stated above are as follows:

(1) Weigh the following components by ratio: pullulan polysaccharide 20-55 weight percent, gellan gum 0.5-4 weight percent, methylglycine-proline moisturizing agent 0.05-2 weight percent, anti-hygroscopic agent 0-1 weight percent, plasticizer 6-40 weight percent.

(2) Add 40-280 weight percent purified water (>80° C.) into the reaction tank at ambient pressure, turn on the blender, set the agitation speed at 40-60 r/min, add gellan gum, amino acid moisturizing agent and anti-hygroscopic agent into the water, stir until the components are well-dispersed.

(3) Keep stirring at speed of 40-60 r/min, add plasticizer and stir until it is well-dispersed.

(4) Add pullulan polysaccharide, stir until it is completely dissolved, keep the gel solution temperature at 70-90° C. for 2-8 h, vacuumize for 20-40 min.

(5) keep the gel solution temperature at 35-75° C., pellet the gel with soft capsule making machine. Finally, soft capsule containing pullulan polysaccharide is obtained.

In the preparation method of hard capsule containing pullulan polysaccharide described above the vacuum degree in procedure (3) is 0.03-0.05 MPa.

In the preparation method of soft capsule containing pullulan polysaccharide described above the vacuum degree in procedure (4) is 0.03-0.05 MPa.

Other additives can be added to the membrane-forming compound stated in this invention as required during the preparation process, such as colorant, opacifier, surfactant, antifoaming agent and so on. There are no special restrictions on the composition of other additives, as long as there is no limitation on the purpose of the invention.

Coating fluid can be added to the surface of hollow hard or soft capsule made from the membrane-forming compound stated in this invention as required to make enteric or colonic-coated capsules.

The beneficial effects of this invention:

1. This invention provides a kind of membrane-forming compound which is suitable for the preparation of hard or soft capsules. Its formulas and techniques are much simpler than current technologies.

2. This invention uses the combination of pullulan polysaccharide and gellan gum, especially high acyl gellan, which results in a rapid gelation of membrane-forming compound and a better gelling effect.

3. This invention introduces methylglycine-proline into the formula. Unexpectedly, it provides both good moisturizing and excellent antioxidant properties These properties further strengthen the storage stability of the product and effectively retard the phenomenon that pullulan polysaccharide capsules get darker after long time storage.

4. This invention add gellan gum as gelling agent and no alkali metal ions are required during the gelation process of capsules which avoids the influence of the disintegration properties of the capsules caused by the addition of alkali metal ions.

5. This invention add methylglycine-proline as moisturizing agent, this natural substance exists in medlar and kelp. It meets people's demand for nature. Furthermore, it has a better moisturizing property and can improve the tenacity of capsule products when comparing with traditional moisturizing agents.

6. This invention add one or combination of stearic acid and lauric acid in any proportion as anti-hygroscopic agent, which mitigates the phenomenon that pullulan polysaccharide capsules are easily to absorb water and turn soft under high humidity environment. Thus, it reduces the demand of the pullulan polysaccharide capsules for strict storage environment.

The Specific Implementation Plan

We will further elaborate this invention with some implementation examples. It should be realized that these examples are used for the explanation not the restriction of this invention. So, this invention is not restricted by the implementation examples. Any technical protocols obtained by equivalent replacement of this invention should be within the scope of protection for this invention.

Moisture absorption of the capsules in the following implementation examples is obtained through the method as follows: Put capsule samples with determined weight into a weighing bottle and keep the weighing bottle open under the environment of 25° C. and 75% relative humidity; Measure the moisture contents of the capsule samples stored for 2, 4, 6, 8 and 10 days respectively and compare them with the initial value; Calculate the water increasing rate of samples, namely moisture absorption. The lower the moisture absorption is, the more stable the sample is in long time storage.

Moisture retention rate of the capsules in the following implementation examples is obtain through the method as follows: Put capsule samples with determined weight into a weighing bottle and keep the weighing bottle open under the environment of 25° C. and 30% relative humidity; Measure the moisture contents of the capsule samples stored for 2, 4, 6, 8 and 10 days respectively and compare them with the initial moisture content; Calculate the water retention rate of samples, namely moisture retention rate. The higher the moisture retention rate is, the more stable the sample is in long time storage.

Oxygen permeation rate of the capsules in the following implementation examples is obtain through the method as follows: Fill hard capsule samples with determined amount of vitamin C, fill soft capsule samples with determined amount of soybean oil and seal the capsules; Put the capsules in an open bottle and stored under the environment of 40° C. and 75% relative humidity; Measure the value of oxidized capsule samples stored for 15, 30, 45, 60, 90 and 120 days respectively which is also called oxygen permeation rate. The lower the oxygen permeation rate is, the more stable the sample is in long time storage.

EXAMPLE 1

Hollow Hard Capsules Containing Pullulan Polysaccharide

First, prepare the materials as follows: pullulan polysaccharide 7600 g, low acyl gellan gum 50 g, methylglycine-proline 5 g, purified water 30000 g.

Preparation method: Add 85° C. purified water 30000 g into the reaction tank, turn on the blender, set the agitation speed at 50 r/min, add low acyl gellan gum 50 g, methylglycine-proline 5 g into the water, stir until the components are well-dispersed; Keep stirring at 50 r/min, add pullulan polysaccharide 7600 g, stir until it is completely dissolved, keep the gel solution at 80° C. for 4 h and vacuumize for 30 min at a vacuum degree of 0.04 MPa; Keep the gel solution at 45° C., and the gelation time is measured to be 25 s; Make capsule shells with a gel dipping mold and dry at 27° C. for 100 min. Finally, hollow hard capsule containing pullulan polysaccharide is obtained.

EXAMPLE 2

Hollow Hard Capsules Containing Pullulan Polysaccharide

First, prepare the materials as follows: pullulan polysaccharide 8000 g, high acyl gellan gum 150 g, methylglycine-proline 6 g, purified water 40000 g.

Preparation method: Add 85° C. purified water 40000 g into the reaction tank, turn on the blender, set the agitation speed at 60 r/min, add high acyl gellan gum 150 g, methylglycine-proline 6 g into the water and stir until the components are well-dispersed; Keep stirring at 50 r/min, add pullulan polysaccharide 8000 g, stir until it is completely dissolved, keep the gel solution at 70° C. for 8 h and vacuumize for 40 min at a vacuum degree of 0.03 MPa; Keep the gel solution at 35° C., and the gelation time is measured to be 16 s; Make capsule shells with a gel dipping mold and dry at 27° C. for 180 min. Finally, hollow hard capsule containing pullulan polysaccharide is obtained.

EXAMPLE 3

Hollow Hard Capsules Containing Pullulan Polysaccharide

First, prepare the materials as follows: pullulan polysaccharide 8000 g, low acyl gellan gum 120 g, methylglycine-proline 10 g, stearic acid 5 g, purified water 35000 g.

Preparation method: Add 85° C. purified water 35000 g into the reaction tank, turn on the blender, set the agitation speed at 55 r/min, add low acyl gellan gum 120 g, methylglycine-proline 10 g and stearic acid 5 g into the water, stir until the components are well-dispersed; Keep stirring at 55 r/min, add pullulan polysaccharide 8000 g, stir until it is completely dissolved, keep the gel solution at 75° C. for 6 h and vacuumize for 20 min at a vacuum degree of 0.04 MPa; Keep the gel solution at 55° C. and the gelation time is measured to be 24 s; Make capsule shells with a gel dipping mold and dry at 28° C. for 150 min. Finally, hollow hard capsule containing pullulan polysaccharide is obtained.

Measure moisture absorption, moisture retention rate and oxygen permeation rate of hollow hard capsules containing pullulan polysaccharide prepared through both Example 3 and traditional method and compare these data. The data are as follows:

| moisture absorption rate/% | | | moisture retention ability/% | | | oxygen permeation rate/g | | |
|---|---|---|---|---|---|---|---|---|
| Storage time | Example 3 | Traditional way | Storage time | Example 3 | Traditional way | Storage time | Example 3 | Traditional way |
| 2 days | 1.2% | 2.7% | 2 days | 98% | 95% | 15 days | 0.7% | 1.7% |
| 4 days | 2.1% | 3.3% | 4 days | 95% | 92% | 30 days | 2.0% | 3.8% |
| 6 days | 3.8% | 5.1% | 6 days | 93% | 88% | 60 days | 4.4% | 6.0% |
| 8 days | 4.4% | 5.9% | 8 days | 88% | 80% | 90 days | 7.3% | 9.2% |
| 10 days | 4.9% | 6.0% | 10 days | 85% | 76% | 120 days | 8.7% | 11.6% |

Control 1

Hollow Hard Capsules Containing Pullulan Polysaccharide

First, prepare the materials as follows: pullulan polysaccharide 8000 g, low acyl gellan gum 120 g, glycerin 10 g, stearic acid 5 g, purified water 35000 g.

Preparation method: Add 82° C. purified water 35000 g into the reaction tank, turn on the blender, set the agitation speed at 55 r/min, add low acyl gellan gum 120 g, glycerin 10 g and stearic acid 5 g into the water and stir until the components are well-dispersed; Keep stirring at 55 r/min, add pullulan polysaccharide 8000 g, stir until it is completely dissolved, keep the gel solution at 75° C. for 6 h and vacuumize for 20 min at a vacuum degree of 0.04 MPa; Keep the gel solution at 55° C., and the gelation time is measured to be 24 s; Make capsule shells with a gel dipping mold and dry at 28° C. for 150 min. Finally, hollow hard capsule containing pullulan polysaccharide is obtained.

Conduct the same performance measurements as Example 3 of hollow hard capsule containing pullulan polysaccharide prepared through Control 1. The data are as follows:

| moisture absorption rate/% | | | moisture retention ability/% | | | oxygen permeation rate/g | | |
|---|---|---|---|---|---|---|---|---|
| Storage time | Example 3 | Control 1 | Storage time | Example 3 | Control 1 | Storage time | Example 3 | Control 1 |
| 2 days | 1.2% | 1.5% | 2 days | 98% | 96% | 15 days | 0.7% | 1.6% |
| 4 days | 2.1% | 2.7% | 4 days | 95% | 94% | 30 days | 2.0% | 3.5% |
| 6 days | 3.8% | 4.5% | 6 days | 93% | 91% | 60 days | 4.4% | 5.6% |
| 8 days | 4.4% | 5.2% | 8 days | 88% | 84% | 90 days | 7.3% | 8.9% |
| 10 days | 4.9% | 5.6% | 10 days | 85% | 80% | 120 days | 8.7% | 11.2% |

EXAMPLE 4

Hollow Hard Capsules Containing Pullulan Polysaccharide

First, prepare the materials as follows: pullulan polysaccharide 7600 g, high acyl gellan gum 100 g, methylglycine-proline 12 g, lauric acid 10 g, purified water 35000 g.

Preparation method: Add 85° C. purified water 35000 g into the reaction tank, turn on the blender, set the agitation speed at 60 r/min, add high acyl gellan gum 100 g, methylglycine-proline 12 g, lauric acid 10 g into the water and stir until the components are well-dispersed; Keep stirring at 60 r/min, add pullulan polysaccharide 7600 g, stir until it is completely dissolved, keep the gel solution at 70° C. for 4 h and vacuumize for 30 min at a vacuum degree of 0.04 MPa; Keep the gel solution at 50° C., and the gelation time is measured to be 15 s; Make capsule shells with a gel dipping mold and dry at 28° C. for 120 min. Finally, hollow hard capsule containing pullulan polysaccharide is obtained.

Measure moisture absorption, moisture retention rate and oxygen permeation rate of hollow hard capsules containing pullulan polysaccharide prepared through both Example 4 and traditional method and compare these data. The data are as follows:

| moisture absorption rate/% | | | moisture retention ability/% | | | oxygen permeation rate/g | | |
|---|---|---|---|---|---|---|---|---|
| Storage time | Example 4 | Traditional way | Storage time | Example 4 | Traditional way | Storage time | Example 4 | Traditional way |
| 2 days | 1.1% | 2.7% | 2 days | 97% | 95% | 15 days | 0.4% | 1.7% |
| 4 days | 1.9% | 3.3% | 4 days | 95% | 92% | 30 days | 2.8% | 3.8% |
| 6 days | 3.5% | 5.1% | 6 days | 91% | 88% | 60 days | 4.7% | 6.0% |
| 8 days | 4.0% | 5.9% | 8 days | 89% | 80% | 90 days | 6.5% | 9.2% |
| 10 days | 4.8% | 6.0% | 10 days | 86% | 76% | 120 days | 7.6% | 11.6% |

Control 2

Hollow Hard Capsules Containing Gelatin

First, prepare the materials as follows: gelatin 7600 g, high acyl gellan gum 100 g, methylglycine-proline 12 g, lauric acid 10 g, purified water 35000 g.

Preparation method: Add 85° C. purified water 35000 g into the reaction tank, turn on the blender, set the agitation speed at 60 r/min, add high acyl gellan gum 100 g, methylglycine-proline 12 g, lauric acid 10 g into the water and stir until the components are well-dispersed; Keep stirring at 60 r/min, add gelatin 7600 g, stir until it is completely dissolved, keep the gel solution at 70° C. for 4 h and vacuumize for 30 min at a vacuum degree of 0.04 MPa; Keep the gel solution at 50° C., and the gelation time is measured to be 15 s; Make capsule shells with a gel dipping mold and dry at 28° C. for 120 min. Finally, hollow hard capsule containing gelatin is obtained.

Conduct the same performance measurements as Example 4. The data are as follows:

| moisture absorption rate/% | | | moisture retention ability/% | | | oxygen permeation rate/g | | |
|---|---|---|---|---|---|---|---|---|
| Storage time | Example 4 | Control2 | Storage time | Example 4 | Control2 | Storage time | Example 4 | Control2 |
| 2 days | 1.1% | 1.2% | 2 days | 97% | 96% | 15 days | 0.4% | 1.8% |
| 4 days | 1.9% | 1.8% | 4 days | 95% | 93% | 30 days | 2.8% | 4.0% |
| 6 days | 3.5% | 3.7% | 6 days | 91% | 90% | 60 days | 4.7% | 6.3% |
| 8 days | 4.0% | 4.2% | 8 days | 89% | 86% | 90 days | 6.5% | 9.7% |
| 10 days | 4.8% | 5.0% | 10 days | 86% | 82% | 120 days | 7.6% | 12.4% |

EXAMPLE 5

Hollow Hard Capsules Containing Pullulan Polysaccharide

First, prepare the materials as follows: pullulan polysaccharide 9000 g, high acyl gellan gum 400 g, methylglycine-proline 200 g, lauric acid 100 g, purified water 55000 g.

Preparation method: Add 85° C. purified water 55000 g into the reaction tank, turn on the blender, set the agitation speed at 40 r/min, add high acyl gellan gum 400 g, methylglycine-proline 200 g, lauric acid 100 g into the water and stir until the components are well-dispersed; Keep stirring at 40 r/min, add pullulan polysaccharide 9000 g, stir until it is completely dissolved, keep the gel solution at 90° C. for 2 h and vacuumize for 20 min at a vacuum degree of 0.05 MPa; Keep the gel solution at 65° C., and the gelation time is measured to be 15 s; Make capsule shells with a gel dipping mold and dry at 29° C. for 120 min. Finally, hollow hard capsule containing pullulan polysaccharide is obtained.

EXAMPLE 6

Hollow Soft Capsules Containing Pullulan Polysaccharide

First, prepare the materials as follows: pullulan polysaccharide 2000 g, low acyl gellan gum 50 g, methylglycine-proline 5 g, glycerin 600 g, purified water 4000 g.

Preparation method: Add 85° C. purified water 4000 g into the reaction tank, turn on the blender, set the agitation speed at 60 r/min, add low acyl gellan gum 50 g, methylglycine-proline 5 g into the water and stir until the components are well-dispersed; Keep stirring at 60 r/min, add glycerin 600 g and stir until it is well-dispersed; Add pullulan polysaccharide 2000 g, stir until it is completely dissolved, keep the gel solution at 70° C. for 8 h and vacuumize for 30 min at a vacuum degree of 0.04 MPa; Keep the gel solution at 55° C. and pellet the gel with soft capsule making machine. Finally, hollow soft capsule containing pullulan polysaccharide is obtained.

EXAMPLE 7

Hollow Soft Capsules Containing Pullulan Polysaccharide

First, prepare the materials as follows: pullulan polysaccharide 3000 g, low acyl gellan gum 200 g, methylglycine-proline 8 g, glycerin 1500 g, purified water 7000 g.

Preparation method: Add 85° C. purified water 7000 g into the reaction tank, turn on the blender, set the agitation speed at 40 r/min, add low acyl gellan gum 200 g, methylglycine-proline 8 g into the water and stir until the components are well-dispersed; Keep stirring at 40 r/min, add glycerin 1500 g and stir until it is well-dispersed; Add pullulan polysaccharide 3000 g, stir until it is completely dissolved, keep the gel solution at 75° C. for 6 h and vacuumize for 40 min at a vacuum degree of 0.04 MPa; Keep the gel solution at 65° C. and pellet the gel with soft capsule making machine. Finally, hollow soft capsule containing pullulan polysaccharide is obtained.

EXAMPLE 8

Hollow Soft Capsules Containing Pullulan Polysaccharide

First, prepare the materials as follows: pullulan polysaccharide 3500 g, low acyl gellan gum 200 g, methylglycine-proline 80 g, stearic acid 30 g, glycerin 1700 g, purified water 8000 g.

Preparation method: Add 85° C. purified water 8000 g into the reaction tank, turn on the blender, set the agitation speed at 50 r/min, add low acyl gellan gum 200 g, methylglycine-proline 80 g, stearic acid 30 g into the water and stir until the components are well-dispersed; Keep stirring at 50 r/min, add glycerin 1700 g and stir until it is well-dispersed; Add pullulan polysaccharide 3500 g, stir until it is completely dissolved, keep the gel solution at 80° C. for 3 h and vacuumize for 40 min at a vacuum degree of 0.03 MPa; Keep the gel solution at 70° C. and pellet the gel with soft capsule making machine. Finally, hollow soft capsule containing pullulan polysaccharide is obtained.

Measure moisture absorption, moisture retention rate and oxygen permeation rate of hollow hard capsules containing pullulan polysaccharide prepared through both Example 8 and traditional method and the data are as follows:

| moisture absorption rate/% | | | moisture retention ability/% | | | oxygen permeation rate/g | | |
|---|---|---|---|---|---|---|---|---|
| Storage time | Example 8 | Traditional way | Storage time | Example 8 | Traditional way | Storage time | Example 8 | Traditional way |
| 2 days | 0.7% | 2.5% | 2 days | 98% | 96% | 15 days | 1.1% | 2.4% |
| 4 days | 2.1% | 3.1% | 4 days | 96% | 93% | 30 days | 2.5% | 3.3% |
| 6 days | 3.3% | 4.1% | 6 days | 95% | 88% | 60 days | 4.3% | 5.8% |
| 8 days | 4.1% | 5.5% | 8 days | 92% | 84% | 90 days | 6.5% | 8.1% |
| 10 days | 4.6% | 5.9% | 10 days | 89% | 81% | 120 days | 8.1% | 10.1% |

EXAMPLE 9

Hollow Soft Capsules Containing Pullulan Polysaccharide

First, prepare the materials as follows: pullulan polysaccharide 5500 g, high acyl gellan gum 400 g, methylglycine-proline 200 g, stearic acid 100 g, glycerin 4000 g, purified water 28000 g.

Preparation method: Add 82° C. purified water 28000 g into the reaction tank, turn on the blender, set the agitation speed at 50 r/min, add high acyl gellan gum 400 g, methylglycine-proline 200 g, stearic acid 100 g into the water and stir until the components are well-dispersed; Keep stirring at 50 r/min, add glycerin 4000 g and stir until it is well-dispersed; Add pullulan polysaccharide 5500 g, stir until it is completely dissolved, keep the gel solution at 90° C. for 2 h and vacuumize for 40 min at a vacuum degree of 0.05 MPa; Keep the gel solution at 75° C. and pellet the gel with soft capsule making machine. Finally, hollow soft capsule containing pullulan polysaccharide is obtained.

In Control 1 stated above, hollow hard capsules were prepared according to Example 3 expect that the moisturizing agent methylglycine-proline was replaced by glycerin. The performance measurements of hollow hard capsule prepared in Control 1 showed that its moisture absorption and moisture retention rate both decreased slightly after 10-day storage when compared to Example 3. However, oxygen permeation rate significantly increased to 11.2% after 120-day storage. Massive experiments have been down and the results show that the combination of pullulan polysaccharide, gellan gum, and methylglycine-proline in this invention, adds prominent anti-oxidation property to methylglycine-proline besides its intrinsic moisture retention property. It results in a low oxygen permeation rate during long-time storage, while the glycerin in Control 1 doesn't show any anti-oxidation property.

In Control 2 stated above, hollow hard capsules were prepared according to Example 4 expect that the pullulan polysaccharide was replaced by a corresponding amount of gelatin. Moisture absorption and moisture retention rate both decreased slightly after 10-day storage. However, oxygen permeation rate significantly increases after 120-day storage. It means that when using gelatin as main component, methylglycine-proline doesn't show any anti-oxidation property. Furthermore, pullulan polysaccharide in Example 4 was replaced by hydroxypropyl methylcellulose as another control experiment in this invention. The performance measurements of hollow hard capsule prepared in this Control showed that its moisture absorption significantly rose up to 5.5% and its moisture retention rate with a value of 84% remained unchanged. In addition, the oxygen permeation rate increased to 13.5% after 120-day storage. This suggests that the storage stability of capsules gets worse evidently, which further verifies that the methylglycine-proline shows anti-oxidation property only in the formula of this invention. Therefore, this invention brings a new direction to the research of the membrane-forming compound using pullulan polysaccharide as main component.

A series of comparative studies, similar to Control 1 and Control 2, were carried out based on Experiment 8. As the results show, when methylglycine-proline is used as moisturizing agent to prepare soft capsules, it also shows anti-oxidation property. This effect also benefits from the combination of pullulan polysaccharide, gellan gum and methylglycine-proline. Nevertheless, replacing the ingredients with other normal moisturizing agent and main component won't bring any improvement to the anti-oxidation property.

In conclusion, methylglycine-proline is used as moisturizing agent in this invention and it unexpectedly improves the anti-oxidation property and the storage stability of the products, which is the special effect achieved by the components provided by this invention.

The invention claimed is:

1. A preparation method of a hard capsule containing pullulan polysaccharide, wherein the method comprises:
   (1) obtaining pullulan polysaccharide 76-90 weight percent, gellan gum 0.5-4 weight percent, methylglycine-proline moisturizing agent 0.05-2 weight percent, anti-hygroscopic agent 0-1 weight percent, based on a total weight of the pullulan polysaccharide, gellan gum, methylglycine-proline moisturizing agent and anti-hygroscopic agent,
   (2) adding the gellan gum, methylglycine-proline moisturizing agent and anti-hygroscopic agent obtained in (1) to a reaction tank containing 300-550 weight percent purified water at a temperature above 80° C. and ambient pressure and at an agitation speed of 40-60 r/min, and stirring until a dispersion is formed,
   (3) adding the pullulan polysaccharide obtained in (1) to the dispersion, stirring until the pullulan polysaccharide is completely dissolved to obtain a gel solution, keeping the gel solution at a temperature of 70-90° C. for 2-8 h and vacuuming for 20-40 min, and
   (4) cooling down the gel solution obtained in (3) to a temperature at 35-75° C., dipping a mold into the gel solution to form a capsule shell, drying the capsule shell at 27-29° C. for 100-180 min, to thereby obtain a hard capsule containing pullulan polysaccharide.

2. A preparation method of a soft capsule containing pullulan polysaccharide, wherein the method comprises:
   (1) obtaining pullulan polysaccharide 20-55 weight percent, gellan gum 0.5-4 weight percent, methylglycine-proline moisturizing agent 0.05-2 weight percent, anti-hygroscopic agent 0-1 weight percent, plasticizer 6-40 weight percent, based on a total weight of the pullulan polysaccharide, gellan gum, methylglycine-proline moisturizing agent, anti-hygroscopic agent and plasticizer, (2) adding the gellan gum, methylglycine-proline moisturizing agent and anti-hygroscopic agent obtained in (1) to a reaction tank containing 40-280 weight percent purified water at a temperature above 80° C. and ambient pressure and at an agitation speed of 40-60 r/min, and stirring until a first dispersion is formed, (3) adding the plasticizer obtained in (1) to the first dispersion obtained in (2) at an agitation speed of 40-60 r/min, to form a second dispersion, (4) adding the pullulan polysaccharide to the second dispersion obtained in (3), stirring until the pullulan polysaccharide is completely dissolved to obtain a gel solution, keeping the gel solution at a temperature of 70-90° C. for 2-8 h and vacuuming for 20-40 min, and (5) cooling down the gel solution obtained in (4) to a temperature at 35-75° C., pelleting the gel solution with a soft capsule making machine, to obtain a soft capsule containing pullulan polysaccharide.

3. The preparation method of hard capsule containing pullulan polysaccharide according to claim 1, wherein the vacuuming (3) is performed at 0.03-0.05 MPa.

4. The preparation method of soft capsule containing pullulan polysaccharide according to claim 2, wherein the vacuuming (4) is performed at 0.03-0.05 MPa.

\* \* \* \* \*